US012765545B2

(12) United States Patent
Rolet et al.

(10) Patent No.: US 12,765,545 B2
(45) Date of Patent: Oct. 20, 2026

(54) PREPARATION OF A DRY BIOMASS EXTRACT RICH IN POLYPHENOLS

(71) Applicant: ANTOFENOL, Montpellier (FR)

(72) Inventors: Fanny Rolet, Saint Pargoire (FR); Ludovic Fabre, Montpellier (FR)

(73) Assignee: ANTOFENOL

(*) Notice: Subject to any disclaimer, the term of this patent is extended or adjusted under 35 U.S.C. 154(b) by 902 days.

(21) Appl. No.: 17/977,195

(22) Filed: Oct. 31, 2022

(65) Prior Publication Data

US 2023/0120978 A1 Apr. 20, 2023

Related U.S. Application Data

(63) Continuation of application No. 16/466,551, filed as application No. PCT/EP2017/084116 on Dec. 21, 2017, now Pat. No. 11,517,015.

(30) Foreign Application Priority Data

Dec. 22, 2016 (FR) ...................................... 1663205

(51) Int. Cl.
*A01N 31/16* (2006.01)
*A23B 2/75* (2025.01)
*A23B 7/154* (2006.01)
*A61K 8/34* (2006.01)
*A61K 31/05* (2006.01)

(52) U.S. Cl.
CPC ................ *A01N 31/16* (2013.01); *A23B 2/75* (2025.01); *A23B 7/154* (2013.01); *A61K 8/347* (2013.01); *A61K 31/05* (2013.01); *A23V 2002/00* (2013.01)

(58) Field of Classification Search
CPC ........ A01N 31/16; A01N 65/00; A01N 37/10; A23B 2/75; A23B 7/154; A61K 8/347; A61K 31/05; A61K 8/9789; A61K 36/87; A23V 2002/00; Y02E 50/10; A61P 17/10; A61P 31/04; A01P 3/00; A61Q 19/00
See application file for complete search history.

(56) References Cited

U.S. PATENT DOCUMENTS

| | | | | |
|---|---|---|---|---|
| 5,989,557 | A | 11/1999 | Bombardelli et al. | |
| 2012/0014210 | A1 | 1/2012 | Wang | |
| 2012/0121742 | A1* | 5/2012 | Mairel .................. | A01N 65/00 424/766 |

FOREIGN PATENT DOCUMENTS

| | | | |
|---|---|---|---|
| CN | 1935947 | A | 3/2007 |
| CN | 102188463 | A | 9/2011 |
| CN | 101816349 | B | 8/2012 |
| CN | 102757512 | A | 10/2012 |
| CN | 103783506 | A | 5/2014 |
| CN | 103961442 | A | 8/2014 |
| CN | 102757509 | B | 12/2014 |
| CN | 104177463 | A | 12/2014 |
| CN | 104256432 | A | 1/2015 |
| CN | 104256641 | B | 8/2015 |
| CN | 103875842 | B | 3/2016 |
| CN | 205759861 | U | 12/2016 |
| CN | 104435135 | B | 1/2017 |
| EP | 2530059 | B1 | 12/2014 |
| FR | 2976062 | B1 | 7/2013 |
| JP | 2001064112 | A | 3/2001 |
| JP | 2004089786 | A | 3/2004 |
| JP | 2008208064 | A | 9/2008 |
| JP | 2014033995 | A | 2/2014 |
| JP | 2015063507 | A | 4/2015 |
| JP | 2016-102192 | A | 6/2016 |
| WO | 2012045923 | A1 | 4/2012 |
| WO | 2015138135 | A1 | 9/2015 |

OTHER PUBLICATIONS

Alexa et al. "Mycoflora and Ochratoxin A Control in Wheat Grain Using Natural Extracts Obtained from Wine Industry By-Products" Int. J. Mol. Sci., 2012, vol. 13, pp. 4949-4967.
Casazza et al. "Extraction of phenolics from Vitis vinifera wastes using non-conventional techniques", J. Food Eng., 2010, vol. 100, pp. 50-55.
Favaron et al. "The Role of Grape Polyphenols on Trans-Resveratrol Activity Against Botrytis Cinerea and of Fungal Lacasse on the Solubility of Putatibe Grape PR Proteins" J. of Plant Pathology, 2009, vol. 91, No. 3, pp. 579-588.
Goupil et al. "Grape marc extract acts as elicitor of plant defence responses" Ecotoxicology, 2012, vol. 21, pp. 1541-1549.
Luque-Rodriguez et al. "Extraction of Polyphenols from Vine Shoots of Vitis vinifera by Superheated Ethanol-Water Mixtures", J. of Agriculture and Food Chemistry, 2006, vol. 54, No. 23, pp. 8775-8781.
Osorio et al. "Biological efficiency of polyphenolic extracts from pecan nuts shell (*Carya Illinoensis*), pomegranate husk (*Punica granatum*) and creosote bush leaves (*Larrea tridentate* Cov.) against plant pathogen fungi", Industrial Crops and Products, 2010, vol. 31, No. 1, pp. 153-157.
Pezet et al. "Glycosylation and oxidative dimerization of resveratrol are respectively associated to sensitivity and resistance of grapevine cultivars to downy mildew", Physiol. Mol. Plant Pathol, 2004, vol. 65, pp. 297-303.
Quan et al. "Microwave-assisted extraction of polyphenols from fresh tea shoot", Sci. Technol. Dev., vol. 9, p. 69-75.
Sanchez et al. "On the Use of the Own Plant's Defence Compounds to Maintain the Post-Harvest Fruit Quality" Open Agric. J., 2008, pp. 43-48.

(Continued)

*Primary Examiner* — Robert A Wax
*Assistant Examiner* — Quanglong N Truong
(74) *Attorney, Agent, or Firm* — BCF LLP

(57) ABSTRACT

The present invention concerns a process for preparing a polyphenol-rich extract of dry plant biomass, in particular parts of vines, the extract obtained and its use for antifungal applications, in particular for the prevention and treatment of fungal infections on fruits and plants after harvest, but also for applications related to its antibacterial and antioxidant properties.

15 Claims, 1 Drawing Sheet

(56) References Cited

OTHER PUBLICATIONS

Daglia "Polyphenoils as antimicrobial agents" Biotechnology, 2012, vol. 23, pp. 174-181.
Faller "Polyphenol content and antioxidant capacity in organic and conventional plant foods", Journal of Food Composition and Analysis, 2010, vol. 23, No. 6, pp. 561-568.
Bouras et al., Optimization of microwave-assisted extraction of polyphenols from Quercus bark, Industrial Crops and Products, 77 (2015), pp. 590-601.
Li et al., Microwave-assistance provides very rapid and efficient extraction of grape seed polyphenols, Food Chemistry, 129(2), 2011, pp. 570-576.
Wang et al., Study of vacuum microwave-assisted extraction of polyphenolic compounds and pigment from Chinese herbs, Journal of Chromatography A, 1198-1199, 2008, pp. 45-53.
Delgado-Torre et al., Comparison of accelerated methods for the extraction of phenolic compounds from different vine-shoot cultivars, Journal of Agricultural and Food Chemistry, 60, 2012, pp. 3051-3060.
Poiana, Enhancing oxidative stability of sunflower oil during convective and microwave heating using grape seed extract, Int. J. Mol. Sci., 13, 2012, pp. 9240-9259.

* cited by examiner

PREPARATION OF A DRY BIOMASS EXTRACT RICH IN POLYPHENOLS

CROSS-REFERENCE TO RELATED APPLICATIONS

The present Application is a Continuation Application of U.S. patent application Ser. No. 16/466,551, filed Jun. 4, 2019, now U.S. Pat. No. 11,517,015, issued Dec. 6, 2022, which is a U.S. national entry under § 371 of PCT/EP2017/084116, filed Dec. 21, 2017, which claims priority from French Patent Application No. 1663205, filed Dec. 22, 2016, the content of each of which is herein incorporated by reference in its entirety.

FIELD OF THE INVENTION

The present invention concerns a process for preparing a polyphenol-rich extract of dry plant biomass, in particular parts of vines, the extract obtained and its use for antifungal applications, in particular for the prevention and treatment of fungal infections on fruits and vegetables after harvest, but also for applications related to its antibacterial and antioxidant properties.

STATE OF THE ART

Polyphenol-rich extracts of plant biomass are known to the skilled person. Much work has focused on extracting biomass to obtain a polyphenol-rich extract, all of which have several disadvantages in terms of the economic viability of the processes, such as low yields or very long extraction times, or limiting their use after extraction, and particularly the use of toxic organic solvents (Goupil et al. 2012, Alexa et al. 2012, Sanchez et al. 2008, Pezet et al. 2004).

Various polyphenol extraction techniques and uses are described in particular in the patents and patent applications US 2012/0021080, U.S. Pat. No. 5,989,557, US 2012/0142105, JP 2016 102192, CN 205 759 861, CN 103 875 842, or in articles by Osorio et al. (2010), Luque-Rodriguez et al. (2006) or Favaron and Lucchetta (2009).

Studies have shown that it is possible to improve biomass extraction processes by microwave, ultrasonic or high-temperature treatments (Quan et al. 2006, CN 104 177 463, CN 104 435 135, CN 102 757 512, CN 104 256 432, CN 104 256 641, CN 103 783 506, CN 102 757 509, CN 101 816 349), for example for the preparation of biodiesel (CN 19 35 947). Some recommend high-temperature treatment under high pressure (Casazza et al. 2010).

However, such high-temperature treatments may alter the properties of the extracts obtained and will not be suitable for the implementation of an industrial process on large volumes of raw materials and solvents.

There is a need for an efficient process for biomass extraction to prepare a polyphenol-rich extract, which is efficient and more economical and does not affect the properties of the biomass concerning its polyphenols.

DISCLOSURE OF THE INVENTION

The present invention concerns a process for preparing an extract of dry plant biomass, in particular a polyphenol-rich extract of *Vitis* sp. comprising (a) a step of extracting the dry biomass by bringing it into contact with an aqueous solvent and (b) a step of recovering the polyphenol-enriched aqueous phase, characterized in that in the extraction step (a), the plant biomass/aqueous solvent mixture is treated simultaneously or sequentially by the combination (i) electromagnetic waves with frequencies ranging from 915 MHz to 28 GHz, and
(ii) stirring of the mixture, and/or
(iii) pressure of 50 to 950 mbar (5,000 to 95,000 Pa).

The invention also concerns the extract obtainable by this process and its use for antifungal applications, in particular for the prevention and treatment of fungal infections on fruit and plants after harvest.

DETAILED DESCRIPTION OF THE INVENTION

The invention concerns the preparation of a polyphenol-rich extract by extraction of a dry biomass with an aqueous solvent.

According to the invention, the term "aqueous solvent" means water or an aliphatic alcohol/water mixture, in particular ethanol/water. In this case, the alcohol/water mixture, in particular ethanol/water, contains 10 to 70 vol. % ethanol. According to a preferred embodiment of the invention, the aqueous solvent is an ethanol/water mixture containing 15 to 40% ethanol.

The plant biomass according to the invention is biomass that is itself known to contain polyphenols, in particular trans-resveratrol, trans-ε-viniferin, trans-piceatannol and trans-vitisin. The skilled person is familiar with this biomass from plants known to contain these polyphenols, used alone or in mixtures, generally dicotyledonous plants such as vines, tea and Japanese knotweed, more particularly vines. For the biomass according to the invention, whole plants or parts of plants, more particularly the aerial parts of plants such as fruits, flowers, leaves, stems, branches or trunk fragments (vines), and mixtures thereof, will be used. If need be, the biomass may also comprise or consist of plant roots.

The biomass is dry, that is to say obtained by drying the plants or parts of plants mentioned above. Drying can be carried out by any method known to the skilled person. Advantageously, drying is achieved by letting the plants or their parts dry in the open air. According to a preferred embodiment of the invention, the plants or their separate parts are put to dry in the open air for from 1 month to 4 years, preferably from 1 to 2 years.

Preferentially, the dry biomass consists of dry parts of plants of the genus *Vitis*, particularly *Vitis vinifera, Vitis labrusca, Vitis riparia, Vitis rupestris, Vitis berlandieri, Vitis amurensis, Vitis coignetiae, Vitis vulpina, Vitis acerilblia, Vitis aestivalis, Vitis rotundifolia* and more particularly *Vitis vinifera*. According to an advantageous embodiment of the invention, the dry biomass comprises or consists of grape canes.

Advantageously, this dried biomass is made up of plant fragments, particularly ground plants or plant parts. Preferentially, the fragments have a particle size of less than 1 cm, more preferentially less than or equal to 5 mm, more preferentially ranging from 1 to 5 mm. This particle size of dry matter fragments/ground dry matter is measured according to the common methods well-known to the skilled person.

The fragmentation of dry plants will be carried out according to the common methods known to the skilled person. According to a particular embodiment of the invention, these fragments are obtained first by shredding the dry matter to obtain 1- to 20-cm fragments which are then ground to obtain the preferably 1- to 5-mm fragments, which correspond to a preferred particle size for extraction.

The skilled person will be able to determine the amounts of extraction solvent to be used in relation to the amount of biomass. Advantageously, the mass ratio of dry plant biomass to aqueous solvent ranges from 1/5 to 1/30, preferentially from 1/10 to 1/20.

The process according to the invention is characterized by the combination of at least two stresses applied simultaneously or successively on the extraction mixture (biomass/solvent):

(i) electromagnetic waves with frequencies ranging from 915 MHz to 28 GHz, and
(ii) stirring, and/or
(iii) pressure of 50 to 950 mbar.

According to the invention, the expression "simultaneous or sequential stirring" means that the microwave treatment and at least the stirring and/or the pressure less than or equal to 950 mbar are carried out at the same time, or one after the other, in particular according to sequences (i)+(ii), or (i)+(iii), or (i)+(ii)+(iii), or [(i), (ii)]+(iii), or [(ii), (iii)]+(i), in any order. In the case of sequential treatment, the skilled person may choose to repeat each sequence several times or to combine different sequences according to a predetermined program, optionally combined with one or more simultaneous treatment sequences.

According to a preferred embodiment of the invention, the three treatments are carried out simultaneously [(i), (ii), (iii)].

Step a) may also comprise an ultrasonic treatment (iv). This treatment may be applied sequentially or simultaneously with treatments (i), (ii) and/or (iii) defined above.

Electromagnetic waves with frequencies ranging from 915 MHz to 28 GHz correspond to waves in the microwave domain. The skilled person will be able to choose the frequency best suited to the implementation of the process, in particular according to the biomass, in order to optimize the extraction process. The frequency of the electromagnetic waves ranges from 915 MHz to 2.45 GHz. Advantageously, the frequency of the electromagnetic waves will be chosen according to known industrial devices for generating electromagnetic waves on an industrial scale, in particular generators of frequencies below 1500 MHz, more advantageously of about 915 MHz.

The skilled person will also be able to choose the wave power best suited to the biomass and to the extracts obtained. The power of the electromagnetic waves ranges from 300 W to 100 kW, more advantageously from 1 to 75 kW.

This power will be chosen in particular according to the volume to be treated and the time required for extraction. According to a preferred embodiment of the invention, the power of the electromagnetic waves is chosen according to the following ratio: for 1 kg of material to be extracted, the power of the electromagnetic waves is from 1 to 10 kW, ideally 2 to 6 kW.

Advantageously, the extraction time will be at least 20 min, or even at least 30 min and preferably less than 125 min, it being understood that too short a time may be associated with over-power conditions that can alter the biomass while too long a time may lead to degradation of the extracted products, and therefore in both cases a risk of polyphenol loss.

The process according to the invention is suitable for use on different volumes of biomass/solvent mixture, in particular on at least 1 L, preferentially at least 5 L. The process according to the invention is particularly suitable for the industrial extraction of dried biomass. Advantageously, the process will be used on biomass/solvent mixture volumes of at least 30 L, which may range to over 50 L or even over 100 L. Depending on the extraction reactors available to the skilled person, the process according to the invention can be used on volumes of more than 200 L.

The biomass/solvent mixture is subjected to stirring (ii), said stirring (ii) being preferentially carried out at the same time as the electromagnetic wave treatment (i). This stirring is important to allow the electromagnetic waves to reach the entire mixture, otherwise only the surface of the mixture would be subjected to the action of these waves.

The skilled person knows the suitable means for carrying out a stirring operation according to the volumes of mixture to be treated. In particular, there are known means of rotating the mixture to be treated, generally by means of rotating blades inside the mixture, or by means of rotating the reactor containing the mixture to be treated. The skilled person may consider other stirring means, such as setting the mixture in motion by bubbling air or inert gas. Preferentially, the stirring is carried out by rotating the mixture at a rotational speed which may range from 3 to 20 revolutions per minute, more preferentially by means of rotating blades inside the mixture.

The skilled person will be able to choose the most suitable means of rotation for implementation in an environment subjected to electromagnetic wave treatment, likely to generate electric arcs.

The process also comprises subjecting the mixture to vacuum (iii), preferably during the electromagnetic wave treatment (i) and stirring (ii).

The skilled person is familiar with the means necessary to obtain a vacuum (or partial vacuum) in an enclosure containing a mixture to be treated. These industrial means make it possible to obtain a pressure ranging from 50 to 950 mbar (5,000 to 95,000 Pa). He or she will be able to choose an appropriate pressure according to the volumes to be treated. In particular, for industrial volumes as described above, it will be advantageous to treat the mixture at a pressure of 50 to 950 mbar (5,000 to 95,000 Pa), preferentially 50 to 500 mbar (5,000 to 50,000 Pa).

Since the process also comprises ultrasonic treatment, the person will be able to choose the frequency as well as the power of the ultrasound. Advantageously, the ultrasonic frequency ranges from 25 kHz to 1 MHz. According to a preferred embodiment of the invention, the ultrasonic power ranges from 200 to 4000 W.

The invention also concerns a process as defined above and in the examples, which comprises an additional step (c) of concentrating the polyphenols by partial or total evaporation of the aqueous solvent.

According to a preferred embodiment of the invention, this concentration (c) is done by freeze-drying the recovered aqueous phase.

According to a particular embodiment of the invention, the dried biomass is subjected, prior to the extraction step (a), to leaching with an appropriate solvent to remove sugars. The skilled person will be able to determine the conditions of this leaching according to the dried biomass and its sugar content.

The removal of sugars, depending on the biomass treated, will be important for obtaining a polyphenol-rich extract with antifungal properties. Indeed, it has been shown that the presence of sugars can have an antagonistic effect on the antifungal activity of polyphenols by promoting fungal growth.

The invention also concerns a polyphenol-rich biomass extract obtainable by the process according to the invention. These extracts have, advantageously, 4 molecules of interest which are polyphenols of the stilbene family. These 4 molecules are trans-piceatannol, trans-resveratrol, trans-ε-viniferin and trans-vitisin. Preferably, the extract contains at least 2 times more trans-ε-viniferin (or at least 2.5 times more) at least 3 times more trans-vitisin (or at least 6 times more) than a conventional ethanol extract.

The invention also concerns a polyphenol-rich biomass extract obtainable by the process according to the invention for a biomass consisting of dry parts of plants of the genus *Vitis*, in particular *Vitis vinifera Vitis labrusca, Vitis riparia, Vitis rupestris, Vitis berlandieri, Vitis amurensis, Vitis coignetiae, Vitis vulpina, Vitis aceridblia, Vitis aestivalis, Vitis rotundifolia* and more particularly *Vitis vinifera*. According to a preferred embodiment of the invention, the polyphenol-rich extract is an extract of grape canes, more particularly of canes of *Vitis vinifera*.

The extracts according to the invention have fungicidal, bactericidal and antioxidant properties, as shown by the examples for an extract of *Vitis vinifera* canes.

The extracts according to the invention, in particular the grape cane extracts, are active as fungicides to control (prevent) the development of harmful fungi in food and agriculture, such as contaminants in canned fruit (*Byssochlamys nivea*), or diseases of fruit trees, vegetables and plants, such as apple canker (*Nectria galligena*), brown rot of fruit trees (*Monilinia fructicola, Monilinia fructigena* and *Monilinia laxa*), carrot blight (*Alternaria* daucil), potato silver scurf (*Helminthosporium solani*), *fusarium* ear blight (*Gibberella zeae*), *fusarium* head blight (*Fusarium culmorum*), *septoria* leaf blotch in wheat (*Mycosphaerella graminicola*), or various rots (including *Penicillium digitatum, Penicillium italicum, Phytophthora syringae* or *Rhizopus stolonifer*).

The invention also concerns a method for fungicidal treatment of plants to prevent or control the development of pathogenic fungi on said plants, said process comprising applying to said plants an effective amount of extract according to the invention, in particular grape cane extract as defined above and in the examples.

The plants treatable with the extracts according to the invention are advantageously plants cultivated for human consumption, such as market gardening, potato crops, field crops such as cereal crops, in particular barley, wheat and maize, soybean or oilseed crops such as rape, sunflower, flax, hemp or cotton. The treatment can also be applied to fruit trees, particularly apple, pear, apricot, peach and vine trees.

Application to the plants is carried out as needed, either as a preventive measure, when climatic conditions are favorable to the development of fungi, or as a curative measure after the appearance of diseases. Application will generally be carried out using standard spraying methods. The skilled person will be able to determine when and how to treat the plants with an extract according to the invention, used alone or in mixture with other products known for their fungicidal properties, such as copper sulfate, Bordeaux mixture, or other plant protection products from the agrochemical industry. Advantageously, the treatment is carried out without using plant protection products from the agrochemical industry, for organic or biodynamic agriculture.

The invention also concerns a method for preventing and/or treating the degradation of fruits and plants after harvest, in particular the development of fungal rot, said process comprising applying to said fruits and plants an appropriate amount of extract obtainable by the process according to the invention as defined above and in the examples.

Through these antioxidant properties, the extracts according to the invention, in particular the grape cane extracts, can also be used to preserve food compositions or cosmetic compositions.

By its ability to delay the oxidation of fruits after harvest, the extract according to the invention, in particular the vine extract, can be used to prevent and/or treat oxidative stress in plants, by application to these plants or to parts of plants, in particular to oxidation-sensitive fruits such as bananas or exotic or tropical fruits such as mango, passion fruit, etc., which are sensitive to oxidative stress when stored at low temperatures, lower than those found in their natural environment. The invention also concerns the use of the extract according to the invention, in particular the grape cane extract, or a composition containing same for the prevention and/or treatment of oxidative stress in plants.

The extract according to the invention, in particular the grape cane extract, can also be used for its antioxidant properties for the prevention and treatment of oxidative stress in humans and animals.

They also have antibacterial activity, particularly on pathogenic Gram-positive bacteria, while preserving commensal bacteria in humans. They are in particular active against bacteria of the genera *Staphylococcus, Listeria, Streptococcus* and *Propionibacterium*, in particular *Propionibacterium acnes*, a pathogen responsible for acne. The extracts according to the invention, in particular the grape cane extracts, have broad-spectrum antimicrobial activity, with greater efficacy against skin pathogens.

The invention therefore concerns an extract according to the invention, particularly a grape cane extract, for use in therapy, in particular for the treatment and prophylaxis of bacterial infections, more particularly for the treatment and prophylaxis of bacterial skin infections, even more particularly for the treatment and prophylaxis of acne.

The invention also concerns a composition comprising an extract obtainable by the process according to the invention as defined above and in the examples and a carrier suitable for use.

It may be an antifungal composition for application to plants before or after harvest, or a pharmaceutical composition. Such compositions are known, and the skilled person will be able to determine the appropriate carrier for this use.

The present invention concerns in particular a plant health composition comprising at least the extract as described above and at least one compatible formulating agent. This plant health composition may be in dry form, for example in powder form or in granular form, or in liquid form, for example in the form of suspension, concentrated or unconcentrated dispersion, gel, emulsion, etc.

The formulating agent is a natural agent or one derived from synthetic chemistry, and conventionally used in plant health compositions.

The formulating agent can be a dispersant, a stabilizer, a surfactant, a preservative, a wetting agent, an adhesion agent, a buffer, a pH regulator, a photoprotector, etc. They can be used alone or in mixture.

The extract obtainable by the process according to the invention as well as the compositions containing same are suitable in particular for use in the prevention and treatment of fungal infections on fruits and plants after harvest.

The process according to the invention comprises the implementation of several techniques combined on the same extraction medium. Each technique (electromagnetic waves, ultrasound, vacuum) and the means for their implementation are well known (WO 2012/045923, EP 2 530 059, FR 2 976 062). The skilled person will be able to adapt existing hydroalcoholic extraction systems for dried biomass to apply these associated treatments.

EXAMPLES

Figure 1:
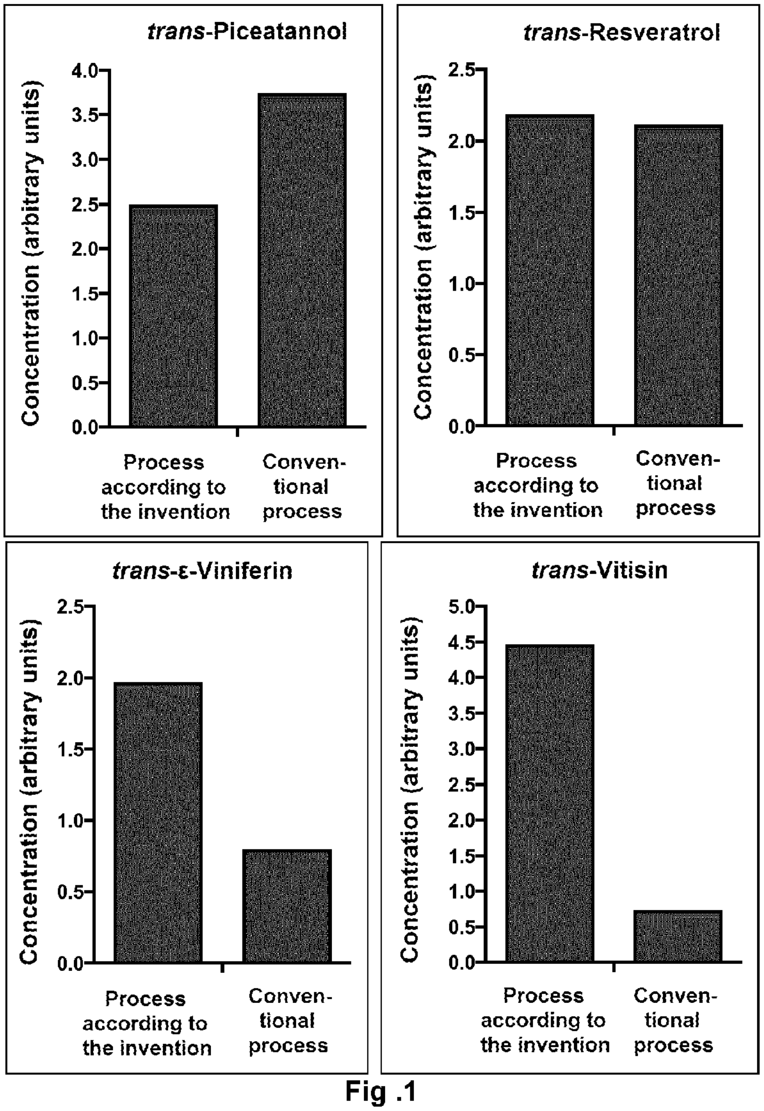
FIG. 1 shows a comparison of the relative amounts of trans-piceatannol, trans-resveratrol, trans-ε-viniferin and trans-vitisin contained in an extract obtained by the process according to the invention and in an extract obtained by a conventional process. The displayed values represent the relative concentrations (in arbitrary units) of each of the 4 molecules, calculated from the areas under the curve of the HPLC peaks.

Example 1, Preparation of a *Vitis vinifera* Cane Eco-Extract

The starting plant material is *Vitis vinifera* cane (August canes). The canes are dried (in the open air or in an oven). Once dry, the canes are first shredded into 2- to 10-cm fragments and then finely ground to a particle size comprised between 1 and 5 mm. The *Vitis vinifera* cane powder thus obtained is extracted in a 30% aqueous or ethanolic solution. The extraction time is comprised between 30 min and 1 h 30 min, preferentially 45 min to 60 min. The techniques used to extract are microwaves, ultrasound, vacuum and simultaneous stirring. The extract thus obtained is vacuum filtered through a 20-micron filter. The extract is then evaporated under vacuum and spray-dried or freeze-dried. The dry extract thus obtained is then stored at room temperature away from light.

Example 2, Chemical Characterization of the *Vitis vinifera* Cane Extract Prepared According to Example 1

Five milligrams of the freeze-dried dry *Vitis vinifera* cane eco-extract obtained according to Example 1 was dissolved in 1 ml of 50% ethanol. The solution is solubilized and then centrifuged for 10 min at 12000 RCF before being injected into a high-performance liquid chromatography/mass spectroscopy (HPLC-MS) system under the following conditions. The volume of extract injected is 25 μl. The migration solvents are ultrapure water (0.1% formic acid) and acetonitrile (0.1% formic acid). The separation is done in 55 min at 1 ml/min according to the following solvent gradient:

| Time (min) | Acetonitrile (%) | Water (%) |
|---|---|---|
| 0 | 5 | 95 |
| 0.1 | 5 | 95.00 |
| 45 | 50 | 50.00 |
| 46 | 100 | 0.00 |
| 51 | 100 | 0.00 |
| 52 | 5 | 95.00 |
| 55 | 5 | 95.00 |

The column used contains a stationary phase grafted with C18 functions. UV detection is performed between 200 and 800 nm. Mass detection is performed by negative-mode ESI. Four major compounds are obtained whose retention times, absorbencies and molecular masses are shown in the table below.

| Compound | Retention time (min) | Maximum absorbance (nm) | Molecular mass (g/mol) |
|---|---|---|---|
| trans-Piceatannol | 19 | 306-323 | 244 |
| trans-Resveratrol | 23 | 306-323 | 228 |
| trans-ε-Viniferin | 30 | 306-323 | 454 |
| trans-Vitisin | 36 | 306-327 | 906 |

The comparison of the content of these 4 compounds with a conventional ethanol extract is shown in FIG. 1.

Example 3, Antifungal Action Against *Botrytis cinerea*

*Botrytis cinerea* spores are deposited at the bottom of the wells of transparent 96-well plates, in which agar nutrient medium has previously been poured.

The freeze-dried dry *Vitis vinifera* cane eco-extract obtained according to Example 1, dissolved at different concentrations (0 g/l, 2.5 g/l, 5 g/I, 10 g/l, 20 g/l and 30 g/l) in 8% ethanol, is then deposited in the wells.

After various incubation times at 21° C. and away from light, the relative density of the mycelium in each well is measured via absorbance at 800 nm. The antifungal efficacy is then calculated from these absorbance values.

Figure 2:
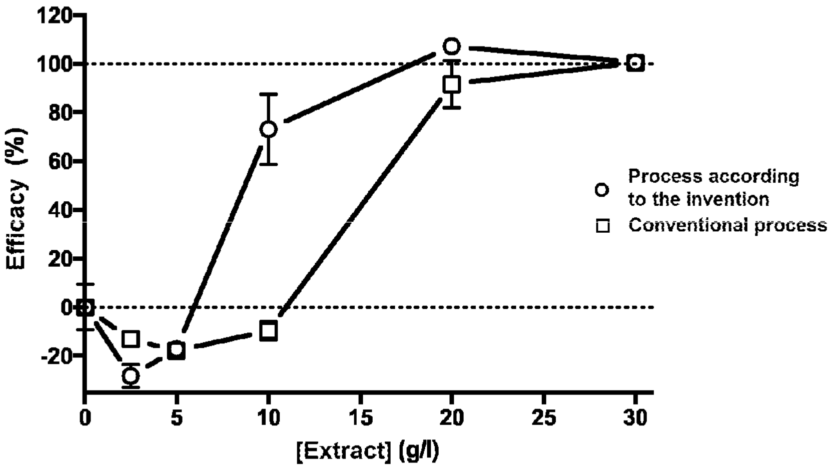
FIG. 2 shows the comparison of the antifungal activity of an extract obtained by the process according to the invention (circles) and an extract obtained by a conventional process (squares). The values displayed are the average, over 3 identical conditions, of the efficacy (0%=normal fungal growth; 100%=no fungal growth) at 4 days post-inoculation, as a function of the extract concentration.

The antifungal efficacy, observed at 4 days of incubation, of an extract obtained with the process according to the invention and an extract obtained with a conventional process is shown in FIG. 2. The results are similar to those presented in FIG. 2 up to at least 15 days of incubation.

Example 4, Antifungal Action

The minimum inhibitory concentrations (MICs) for 100% efficiency up to 240 hours were measured with the extract according to Example 2 on different fungal strains. The results are detailed in the Table below.

| Fungus | MIC g/L |
|---|---|
| *Byssochlamys nivea* | 28 |
| *Nectria galligena* | 13 |
| *Monillinia laxa* | 8 |
| *Alternaria daucil* | 7 |
| *Helminthosporium solani* | 2 |
| *Gibberella zeae* | 9 |
| *Fusarium culmorum* | 9 |
| *Mycosphaerella graminicola* | 1 |

Example 5, Antibacterial Action

The MICs of the extract of Example 2 were determined for different bacterial species. The tests are performed on 27 bacterial strains listed in the table below. The study is conducted in rich nutrient media, with a concentration of tested colonies calibrated at $5 \cdot 10^5$-$10^6$ CFU/mL.

| Bacteria | MIC mg/ML |
|---|---|
| Bacillales | |
| *Bacillus cereus* | 0.234 |
| *Bacillus subtilis* | 0.938 |
| *Staphylococcus aureus* | 0.469 |
| *S. aureus* MR (MRSA) | 0.469 |
| *Staphylococcus epidermidis* | 0.234 |
| *Listeria monocytogenes* | 0.469 |
| *Lactobacillus* | |
| *Enterococcus hirae* | 0.469 |
| *Lactobacillus acidophilus* | 7.5 |
| *Lactobacillus casei* | 7.5 |
| *Lactobacillus plantarum* | >7.5 |
| *Streptococcus mutans* | 3.75 |
| *Streptococcus pyogenes* | 0.234 |
| *Streptococcus suis* | 0.469 |
| Selenomonadales | |
| *Veillonella dispar* | 0.938 |
| Clostridiales | |
| *Clostridium difficile* | 0.938 |
| Enterobacteriales | |
| *Salmonella enterica typhimurium* | 1.875 |
| *Escherichia coli* | 7.5 |
| *Yersinia enterocolitica* | 3.75 |
| Vibrionales | |
| *Vibrio cholerae* | 0.938 |
| *Vibrio anguillarum* | >7.5 |
| Campylobacterales | |
| *Campylobacter jejuni* | 1.875 |
| Bacteroidales | |
| *Bacteroides fragilis* | 3.75 |
| Bifidobacteriales | |
| *Bifidobacterium breve* | 1.875 |
| *Bifidobacterium lactis* | 1.875 |
| *Bifidobacterium longum longum* | 0.938 |
| Actinomycetales | |
| *Actinomyces naeslundii* | 3.75 |
| *Propionibacterium acnes* | 0.117 |

The extract of Example 2 shows inhibitory activity on all strains tested except *Lactobacillus plantarum* and *Vibrio* anguillarum. The most sensitive strain tested is *P. acnes*, a pathogen responsible for acne. Finally, bacteria of the order Bacillales, *Enterococcus* sp. and certain *Streptococcus* sp., are the most sensitive to the extract according to Example 2. On the other hand, the other strains tested are less sensitive, in particular the beneficial bacteria *Bifidobacterium* sp. and *Lactobacillus* sp., as well as Gram-negative bacteria.

The extract of Example 2 is a broad-spectrum antimicrobial with greater efficacy on skin pathogens.

Example 6, Antioxidant Activity

The antioxidant activity of the extract of Example 2 is studied by comparing the condition of the skin of bananas kept in the open air with or without application of the extract of Example 2 at 7 days and 9 days after application.

Without the application of extract of Example 2, banana peels covered with brown spots characteristic of their oxidation are observed at 7 days, while the peels of treated bananas are slightly affected (1 characteristic spot).

At 9 days, oxidation of the skin of untreated bananas continues with entire blackened areas from the covering of spots observed at 7 days, while the skin of treated bananas changes little from the observation at 7 days.

This antioxidant activity observed on bananas shows the interest of the extract according to the invention to treat oxidative stress in plants, especially for exotic or tropical fruits.

REFERENCES

Alexa, E., Poiana, M. A. & Sumalan, R. M. Mycoflora and ochratoxin a control in wheat grain using natural extracts obtained from wine industry by-products. *Int. J. Mol. Sci.* 13, 4949-4967 (2012).

Casazza, A. a., Aliakbarian, B., Mantegna, S., Cravotto, G. & Perego, P. Extraction of phenolics from *Vitis vinifera* wastes using non-conventional techniques. *J. Food Eng.* 100, 50-55 (2010).

Favaron & Lucchetta, Role of grape polyphenols on trans-resveratrol activity against *Botrytis Cinerea* and of fungal Lacasse on the solubility of putatibe grapepr proteins *J. of Plant Pathology* vol 91, n° 3, 579-588 (2009)

Goupil, P. et al. Grape marc extract acts as elicitor of plant defence responses. *Ecotoxicology* 21, 1541-1549 (2012).

Luque-Rodiguez & al. Extraction of polyphenols from Vine shoots of *Vitis vinifera* by Superheated Ethanol-Water Mixtures *J. of Agriculture and Food Chemistry* vol 54, no 23, 8775-8781 (2006)

Osorio & al Biological efficiency of polyphenolic extracts from pecan nuts shell (*Carya* Illinoensis), pomegranate husk (Punica granatum) and creosote bush leaves (Larrea tridentate Cov.) against plant pathogen fungi Industrial Crops and Products, col 31, no 1, 153-157 (2010), Pezet, R., Gindro, K., Viret, O. & Spring, J. L. Glycosylation and oxidative dimerization of resveratrol are respectively associated to sensitivity and resistance of grapevine cultivars to downy mildew. *Physiol. Mol. Plant Pathol.* 65, 297-303 (2004).

Quan, P. T., Hang, T. Van, Ha, N. H., De, N. X. & Tuyen, T. N. Microwave-assisted extraction of polyphenols from fresh tea shoot. *Sci. Technol. Dev.* 9, 69-75 (2006).

Sanchez, J. B. J., Orea, J. M., Gonzalvez, A. G. & Urena, A. G. On the Use of the Own Plant's Defence Compounds to Maintain the Post-Harvest Fruit Quality. *Open Agric. J.* 43-48 (2008).

CN 104 177 463, CN 104 435 135, CN 102 757 512, CN 104 256 432, CN 104 256 641, CN 103 783 506, CN 102 757 509, CN 101 816 349, CN 19 35 947, CN 205 759 861, CN 103 875 842

EP 2 530 059

FR 2 976 062

JP 2016 102192

WO 2012/045923,

U.S. Pat. No. 5,989,557, US 2012/0142105

The invention claimed is:

1. A polyphenol-rich extract of *Vitis* sp. comprising trans-piceatannol, trans-resveratrol, trans-ε-viniferin and trans-vitisin wherein said extract is obtained by a process comprising:

(a) extracting dry grape canes by bringing them into contact with an aqueous solvent to generate a polyphenol-enriched aqueous phase, (b) recovering the polyphenol-enriched aqueous phase, (c) passing the polyphenol-enriched aqueous phase through a filter, producing a filtered extract, and (d) concentrating polyphenols in the filtered extract by partial or total evaporation of the aqueous solvent, wherein the dry grape canes have a particle size of from 1 mm to 1 cm, and wherein in the extraction step (a), the dry grape canes/aqueous solvent mixture is treated simultaneously by:

(i) electromagnetic waves with frequencies ranging from 915 MHz to 28 GHz, and (ii) stirring of the mixture by rotating the dry grape canes/aqueous solvent mixture at a rotational speed ranging from 3 to 20 revolutions per minute;

wherein the polyphenol-rich extract contains at least 2 times more trans-ε-viniferin and at least 3 times more trans-vitisin than a conventional ethanol extract obtained by the process without steps (i) and (ii).

2. The polyphenol-rich extract according to claim 1, wherein in the process of obtaining said extract, the aqueous solvent is water or an ethanol/water mixture comprising from 10 to 70 vol. % ethanol.

3. The polyphenol-rich extract according to claim 2, wherein in the process of obtaining said extract, the aqueous solvent is an ethanol/water mixture comprising from 30 to 50 vol. % ethanol.

4. The polyphenol-rich extract according to claim 1, wherein in the process of obtaining said extract, the mass ratio of dry plant biomass to aqueous solvent is from 1/5 to 1/30.

5. The polyphenol-rich extract according to claim 1, wherein in the process of obtaining said extract, the mass ratio of dry plant biomass to aqueous solvent is from 1/10 to 1/20.

6. The polyphenol-rich extract according to claim 1, wherein in the process of obtaining said extract, the frequency of the electromagnetic waves ranges from 915 MHz to 2.45 GHz.

7. The polyphenol-rich extract according to claim 1, wherein in the process of obtaining said extract, the power of the electromagnetic waves ranges from 300 W to 100 kW.

8. The polyphenol-rich extract according to claim 7, wherein in the process of obtaining said extract, the power of the electromagnetic waves ranges from 1 to 75 kW.

9. The polyphenol-rich extract according to claim 1, wherein in the process of obtaining said extract, said concentrating in step (d) is achieved by freeze-drying the filtered extract.

10. A fungicidal composition comprising the polyphenol-rich extract of *Vitis* sp. comprising trans-piceatannol, trans-resveratrol, trans-ε-viniferin and trans-vitisin according to claim 1 and a carrier.

11. A method for fungicidal treatment of plants to prevent or control the development of pathogenic fungi on said plants, said method comprising applying to said plants an effective amount of the polyphenol-rich extract according to claim 1 or the fungicidal composition according to claim 10.

12. A method for preventing and/or treating the degradation of fruits and plants from pathogenic fungi after harvest, said method comprising applying to said fruits and plants an effective amount of the polyphenol-rich extract according to claim 1.

13. A method for preventing and/or treating the degradation of fruits and plants from pathogenic fungi after harvest, said method comprising applying to said fruits and plants an effective amount of the fungicidal composition according to claim 10.

14. The polyphenol-rich extract of claim 1, wherein the *Vitis* sp. is *Vitis vinifera, Vitis labrusca, Vitis riparia, Vitis rupestris, Vitis berlandieri, Vitis amurensis, Vitis coignetiae, Vitis vulpina, Vitis acerifolia, Vitis aestivalis* or *Vitis rotundifolia.*

15. The polyphenol-rich extract of claim 1, wherein the *Vitis* sp. is *Vitis vinifera.*

* * * * *